United States Patent [19]

Cale, Jr. et al.

[11] 3,966,957

[45] June 29, 1976

[54] METHOD FOR CONTROLLING EMESIS WITH N-(1-SUBSTITUTED-3-PYRROLIDINYL)-BENZAMIDES AND THIOBENZAMIDES

[75] Inventors: Albert Duncan Cale, Jr., Mechanicsville; Charles Arthur Leonard, Richmond, both of Va.

[73] Assignee: A. H. Robins Company, Incorporated, Richmond, Va.

[22] Filed: Oct. 25, 1974

[21] Appl. No.: 518,123

Related U.S. Application Data

[60] Division of Ser. No. 340,417, March 12, 1973, abandoned, and a continuation-in-part of Ser. No. 240,840, April 3, 1972, abandoned.

[52] U.S. Cl. ............................................. 424/274
[51] Int. Cl.² ......................................... A61K 31/40
[58] Field of Search ................................... 424/274

[56] References Cited
UNITED STATES PATENTS

| | | | |
|---|---|---|---|
| 3,342,826 | 9/1967 | Miller et al. ........................ | 424/274 |
| 3,415,934 | 12/1968 | Thominet ........................... | 424/274 |
| 3,577,440 | 5/1971 | Lunsford et al. ................... | 424/274 |

*Primary Examiner*—Donald B. Moyer

[57] ABSTRACT

A method is disclosed for controlling emesis utilizing N-(1-substituted-3-pyrrolidinyl)benzamides and thiobenzamides of the formula:

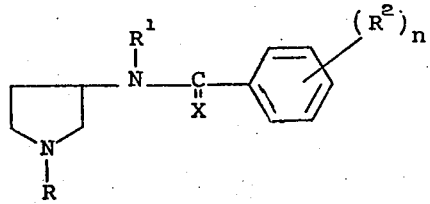

wherein R is cycloalkyl, phenyl and phenyllower-alkyl; $R^1$ is hydrogen, lower alkyl of 1 to 8 carbon atoms and phenyl; $R^2$ is halogen, lower-alkyl, lower-alkoxy, amino, nitro, monoalkylamino, dialkylamino, mercaptomethyl, acetamido, sulfamoyl, cyano, hydroxy, benzyloxy, and trifluoromethyl; X is oxygen and sulfur; n is an integer from zero to three inclusive and pharmaceutically acceptable acid addition salts thereof. The benzamide compounds wherein R is cyclohexyl and $R^1$ is lower-alkyl are particularly effective as antiemetics and have minimal side effects.

33 Claims, No Drawings

METHOD FOR CONTROLLING EMESIS WITH N-(1-SUBSTITUTED-3-PYRROLIDINYL)BENZAMIDES AND THIOBENZAMIDES

The present application is a continuation-in-part application of our copending application Ser. No. 240,840, filed Apr. 3, 1972 now abandoned. This is a division, of application Ser. No. 340,417, filed Mar. 12, 1973 now abandoned.

The present invention is concerned with heterocyclic compounds useful as antiemetics and is particularly concerned with certain N-(3-pyrrolidinyl)benzamides and thiobenzamides, compositions thereof and methods for employing the compositions in controlling emesis in warm blooded animals with minimal side effects.

U.S. Pat. No. 3,342,826 discloses benzamido heterocyclic compounds which are alleged to have great potency in antiemetic tests. In one particular embodiment of said patent the heterocyclic moiety is a pyrrolidine ring having lower alkyl and allyl radicals attached to the secondary nitrogen atom of the pyrrolidine ring and lower alkoxy radicals at the ortho position of the benzamido moiety. The compounds possess the undesirable effect of producing catalepsy at rather low dosages. We have discovered that when the radical attached to the secondary nitrogen atom of the pyrrolidine ring is a cycloalkyl radical such as cyclopentyl, cyclododecyl or cyclohexyl, phenyl, or a phenyllower-alkyl radical, the compounds possess desirable antiemetic properties and furthermore the presence of a lower alkoxy radical at the ortho position of the benzamido moiety is not necessary for antiemetic activity. We have further discovered that when the radical attached to the secondary nitrogen atom of the pyrrolidine ring is cyclohexyl, the antiemetic activity is generally enhanced compared to the prior art compounds and, furthermore, when the amido nitrogen has a lower alkyl substituent, the compounds are free of the undesirable side effects of catalepsy. Thus, the compounds of the present invention which have the combination of a cyclohexyl radical on the secondary nitrogen atom of the pyrrolidine ring and a lower alkyl radical on the amido nitrogen represent a preferred embodiment. We have also discovered that when the preferred compounds are administered to animals in dosages for emesis control, side effects such as behavioral, tranquilizing, depressant, antihistaminic and drug potentiating effects are minimal. Some of the compounds of the present invention have been disclosed to have analgetic and antidepressant properties in U.S. Pat. No. 3,577,440.

The antiemetic compounds of the present invention are primarily benzamides illustrated generally by the following formula:

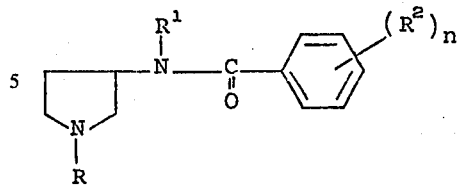

Formula I wherein;
R is cycloalkyl, phenyl and phenyllower-alkyl,
$R^1$ is hydrogen, lower-alkyl of 1 to 8 carbons and phenyl,
$R^2$ is halogen, lower-alkyl, lower-alkoxy, amino, nitro, monoalkylamino, dialkylamino, mercaptomethyl, acetamido, sulfamoyl, cyano, hydroxy, benzyloxy, and trifluoromethyl,
n is an integer from zero to three inclusive, and
pharmaceutically acceptable acid addition salts thereof.

Additional antiemetic compounds of the present invention include thiobenzamides illustrated generally by the following formula:

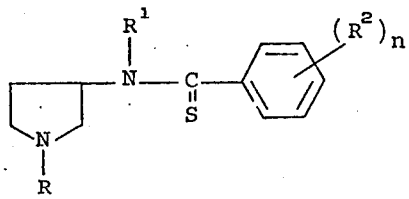

Formula II wherein;
R is cycloalkyl,
$R^1$ is hydrogen and lower alkyl of 1 to 8 carbon atoms,
$R^2$ is nitro, amino, halogen, sulfamoyl and lower-alkoxy,
n is an integer from zero to three inclusive, and
pharmaceutically acceptable acid addition salts thereof.

The nontoxic pharmaceutically acceptable acid addition salts of the basic compounds of Formula I are also included within the scope of this invention, since such salts can likewise be used as antiemetics. Both organic and inorganic acids can be employed to form the pharmaceutically acceptable acid addition salts, illustrative acids being sulfuric, nitric, phosphoric, citric, acetic, lactic, tartaric, sulfamic, succinic, fumaric, maleic, hydrochloric, hydrobromic, benzoic, and the like. The salts are prepared by methods well known to the art.

It is, therefore, a primary object of the present invention to provide a method for controlling emesis. Another object is to provide a method for controlling emesis with minimal side effects. A still further object is to provide novel compositions useful as antiemetics.

Additional objects and advantages of the present invention will be apparent to one skilled in the art and still others will become apparent from the following description of the best mode of carrying out the present invention and from the appended claims.

In the definition of the symbols in Formula I given above, and where they appear elsewhere throughout the claims and specification hereof, the terms have the following significance.

The term "cycloalkyl" as used herein includes primarily cyclic alkyl radicals containing four up to twelve carbon atoms inclusive and includes such groups as cyclobutyl, cyclopentyl, cyclohexyl, cycloheptyl and the like.

The term "halogen" includes fluorine, chlorine, bromine and iodine.

The term "phenyl" as used herein shall mean a phenyl radical or a phenyl radical which is substituted by a radical or more than one radical which are not reactive or otherwise interfering under the conditions of reaction described herein such as lower-alkoxy, lower-alkoxy, trifluoromethyl, halo, and the like. The substituted phenyl radicals have preferably no more than three substituents such as those given above and, furthermore, these substituents can be in various available positions of the phenyl nucleus and when more than one substituent is present, may be the same or different and may be in various position combinations relative to each other. The lower-alkyl and lower-alkoxy substituents each have preferably from one to four carbon atoms which can be arranged as straight or branched chains. Examples of the preferred substituents are methyl, ethyl, propyl, butyl, fluoro, bromo, chloro, iodo, amino, methoxy, ethoxy, propoxy, butoxy, and trifluoromethyl radicals.

The term "lower-alkyl" includes straight and branched chain radicals containing 1 to 8 carbon atoms as, for example, methyl, ethyl, propyl, isopropyl, n-butyl, isobutyl, tertiary butyl, amyl, isoamyl, n-hexyl, n-heptyl, and n-octyl radicals.

Included in the term "phenyllower-alkyl" are such groups as benzyl, phenethyl and the like.

METHOD OF PREPARATION

The preparation of the benzamido compounds of Formula I may be accomplished by mixing and reacting the appropriately substituted 3-aminopyrrolidine (III) with a substituted benzoyl chloride (IV). The reaction sequence is illustrated by the following:

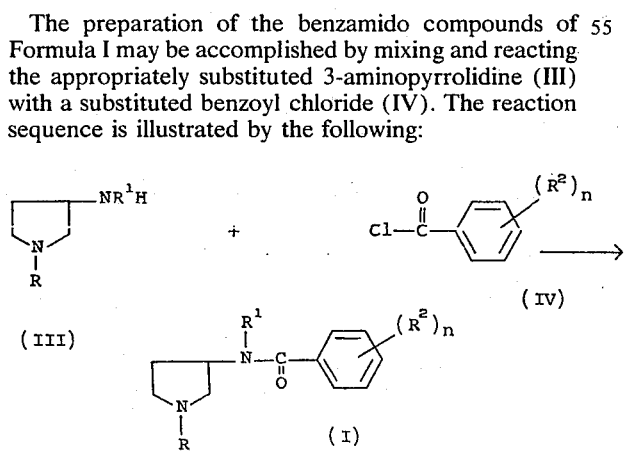

wherein R, $R^1$ and $n$ are defined above and $R^2$ is as defined above except it cannot be primary amino or acetamido.

Compounds of Formula I wherein $R^2$ is primary amino and acetamido are prepared by catalytic hydrogenation of a compound of Formula I wherein $R^2$ is nitro and acylation of the resultant amino compound.

The 3-aminopyrrolidine starting materials (III) are prepared by the procedures disclosed in U.S. Pat. No. 3,337,580. The substituted benzoyl chlorides (IV) are either known compounds or they can be prepared by procedures well known to the art.

The preparation of the thiobenzamido compounds of Formula II may be accomplished by mixing and reacting a benzamido compound of Formula I with a mixture of phosphorus pentasulfide ($P_2S_5$) and potassium sulfide ($K_2S$) or by mixing and reacting an appropriately substituted 3-aminopyrrolidine (III) with an appropriately substituted benzaldehyde (V) and sulfur. The reaction sequences are illustrated by the following:

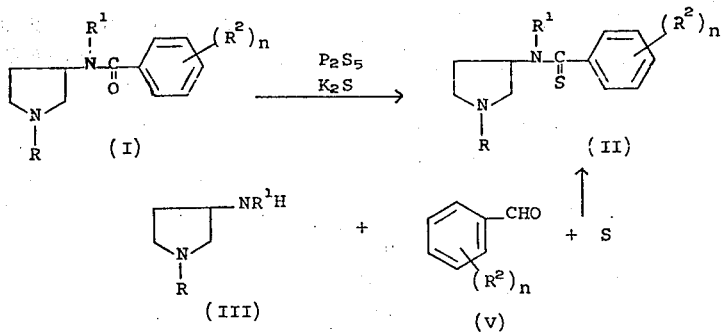

The compounds of Formula I which are the active ingredients in the pharmaceutical compositions of the present invention can be prepared according to the procedures as shown in Examples 1–7 and 9. Examples 10–49 are prepared using the procedures given in Examples 1–7 and 9. Examples 8(A) and 8(B) are N(1-alkyl-3-pyrrolidinyl)benzamides and are not included within the scope of the present invention. They are representative of compounds in the prior art and are included for comparative pharmacological evaluation with the compounds of the present invention.

In the structural formulae of Formula I and Formula II centers of asymmetry are present in the compounds of the present invention. The compounds can be resolved into their optically active forms by combining the compounds with optically active organic acids and separating the optically active forms by fractional crystallization. The optically active forms are included within the scope of the present invention.

EXAMPLE 1

N-(1-Cyclohexyl-3-pyrrolidinyl)-3-bromobenzamide.

To 16.2 g. (0.1 mole) of 3-amino-1-cyclohexylpyrrolidine in 100 ml. of chloroform was added with stirring 15.1 g. (0.07 mole) of 3-bromobenzoyl chloride. After stirring for one hour, the solution was extracted with dilute sodium hydroxide. The chloroform layer was dried over anhydrous sodium sulfate and concentrated. The residue was recrystallized twice from ethyl acetate-isopropyl ether. The impure crystalline material was then partitioned between ethyl acetate and dilute hydrochloric acid. The acid layer was made basic with sodium hydroxide and extracted with chloroform. The chloroform layer was dried over anhydrous sodium sulfate, concentrated, and the residue recrystallized from ethyl acetate-isopropyl ether solvent. The yield was 9.1 g. (36.6%); m.p. 128°–130°C.

Analysis: Calculated for $C_{17}H_{23}BrN_2O_3$: C,58.13; H,6.60; N,7.97. Found: C,58.06; H,6.61; N,7.93.

EXAMPLE 2

N-(1-Cyclohexyl-3-pyrrolidinyl)-2-fluorobenzamide hydrochloride.

To 19.5 g. (0.117 mole) of 3-amino-1-cyclohexylpyrrolidine in 100 ml. of chloroform was added dropwise 11.6 g. (0.074 mole) of o-fluorobenzoyl chloride in 100 ml. of chloroform. The solution was concentrated in vacuo and the residue partitioned between ethyl acetate containing 10% isopropyl ether and dilute hydrochloric acid. The acid layer was made basic with dilute sodium hydroxide and extracted with chloroform. The chloroform solution was dried over sodium sulfate, concentrated and the residue crystallized twice from ligroin. The yield was 13 g. (82%); m.p. at 204°–206°C.

Analysis: Calculated for $C_{17}H_{24}ClFO$: C,62.47; H,7.40; N,8.57. Found: C,62.28; H,7.46; N,8.50.

When in the procedure of Example 2 there are substituted for 3-amino-1-cyclohexylpyrrolidine equal molar amounts of:

1-cyclohexyl-3-(3-trifluoromethylanilino)pyrrolidine;
1-cyclohexyl-3-(4-chloroanilino)pyrrolidine; and
1-p-chlorophenyl-3-(2-methoxyanilino)pyrrolidine;
there are obtained:
2-fluoro-N-(1-cyclohexyl-3-pyrrolidinyl)-N-(3-trifluoromethylphenyl)benzamide hydrochloride;
2-fluoro-N-(1-cyclohexyl-3-pyrrolidinyl)-N-(4-chlorophenyl)benzamide hydrochloride; and
2-fluoro-N-(1-p-chlorophenyl-3-pyrrolidinyl)-N-(2-methoxyphenyl)benzamide hydrochloride.

EXAMPLE 3

N-(1-Phenyl-3-pyrrolidinyl)-4-nitrobenzamide

A solution of 6.9 g. (0.037 mole) of p-nitrobenzoyl chloride in 30 ml. of chloroform was added dropwise at room temperature to a stirred mixture of 6 g. (0.037 mole) of 1-phenyl-3-aminopyrrolidine in 30 ml. of chloroform and 10 g. of potassium carbonate in 30 ml. of water. After addition, the mixture was stirred an additional 30 minutes. The chloroform layer was separated, dried over magnesium sulfate and evaporated to a solid. Recrystallization of the crude product from ethanol-water solution gave 10.6 g. (92%) of orange solid which melted at 153°–155°C.

Analysis: Calculated for $C_{17}H_{17}N_3O_3$: C,65.58; H,5.50; N,13.50. Found: C,65.40; H,5.42; N,13.41.

EXAMPLE 4

4-Amino-N-(1-cyclohexyl-3-pyrrolidinyl)-N-methylbenzamide Cyclohexanesulfamate

4-Nitro-N-(1-cyclohexyl-3-pyrrolidinyl)-N-methylbenzamide was prepared from 15 g. (0.085 mole) of 1-cyclohexyl-3-methylaminopyrrolidine and 15 g. (0.08 mole) p-nitrobenzoyl chloride. The 4-nitro-N-(1-cyclohexyl-3-pyrrolidinyl)-N-methylbenzamide was converted to the fumarate salt (8.4 g., 24%) by precipitation with fumaric acid from isopropanol-isopropyl ether. The fumarate salt was dissolved in 95% ethanol and hydrogenated at three atmospheres of hydrogen over Raney Nickel for about two hours. The mixture was filtered, the filtrate concentrated and the residue partitioned between dilute sodium hydroxide and chloroform. The chloroform layer was dried and concentrated and the residue treated with hexamic acid in isopropanol-isopropyl ether. Recrystallization from the same solvent gave 5.2 g. (13.5% overall) of the salt melting 196°–199°C.

Analysis: Calculated for $C_{24}H_{40}N_4O_4S$: C,59.97; H,8.39; N,11.66. Found: C,59.84; H,8.39; N,11.55.

EXAMPLE 5

N-(1-Benzyl-3-pyrrolidinyl)-3,4,5-trimethoxybenzamide

A mixture of 1.8 g. (0.01 mole) of 3-amino-1-benzylpyrrolidine, 2.4 g. (0.01 mole) of 3,4,5-trimethoxybenzoyl azide, and 25 ml. of dry benzene was stirred 16 hours at room temperature followed by stirring for one hour at about 60°C. The mixture was cooled and 50 ml. of isopropyl ether added to the mixture. The crude crystalline product was separated by filtration and recrystallized from ethyl acetate-isopropyl ether mixture, giving 2.2 g. (60% yield). The melting point of the product after a second recrystallization from the same solvent was 128°–129°C.

Analysis: Calculated for $C_{21}H_{26}N_2O_4$: C,68.09; H,7.08; N,7.56. Found: C,68.00; H,7.26; N,7.62.

EXAMPLE 6

N-(1-Cyclohexyl-3-pyrrolidinyl)-p-dimethylamino-N-methylbenzamide Fumarate

To 16.5 g. (0.1 mole) of 4-dimethylaminobenzoic acid in 100 ml. of carbon tetrachloride was added dropwise with stirring 37.4 g. (0.11 mole) of trioctylphosphene. After the solution had stirred an additional 15 minutes, 18.5 g. (0.1 mole) of 1-cyclohexyl-3-methylaminopyrrolidine was added with continued stirring. The crystalline product which precipitated after an additional one-hour stirring time was separated by filtration and recrystallized from methyl isobutyl ketone containing a small amount of methanol. The impure material was partitioned between chloroform and dilute sodium hydroxide, the chloroform solution was concentrated and the residue converted to the fumarate salt in a mixture of isopropanol ether-isopropanol. After recrystallizing from isopropanol-methanol, 6.1 g. (14%) product was obtained which melted at 185°–186°C.

Analysis: Calculated for $C_{24}H_{35}N_3O_5$: C,64.70; H,7.92; N,9.43. Found: C,64.29; H,8.00; N,9.43.

EXAMPLE 7

N-(1-Cyclohexyl-3-pyrrolidinyl)-4-acetamidobenzamide

To a suspension of 8.6 g. (0.3 mole) of p-amino-N-(1-cyclohexyl-3-pyrrolidinyl)benzamide in 50 ml. of chloroform was added dropwise with stirring, 3.37 g. (0.03 mole) of acetic anhydride. The mixture was stirred for 30 minutes and the solution extracted with dilute sodium hydroxide. The chloroform layer was dried over sodium sulfate, filtered and concentrated. The residue was dissolved in hot ethyl acetate and an equivalent amount of isopropyl ether added to precipitate the product. After recrystallizing from the same solvent, 5.1 g. (50%) of product melting at 184°–186°C. was obtained.

Analysis: Calculated for $C_{19}H_{27}N_3O_2$: C,69.27; H,8.26; N,12.76. Found: C,69.22; H,8.28; N,12.70.

EXAMPLE 8(A)

N-(1-Methyl-3-pyrrolidinyl)benzamide Fumarate

To 10 g. (0.1 mole) of 3-amino-1-methylpyrrolidine in 100 ml. of chloroform, 13.6 g. (0.1 mole) of benzoyl chloride was added at a rapid drop with stirring. The solution was stirred for an additional 0.5 hour, extracted with dilute sodium hydroxide, dried over sodium sulfate and concentrated. The fumarate salt was crystallized from isopropyl alcohol and recrystallized from isopropyl alcohol-methanol. Yield of product was 14.8 g. (46%); m.p. 164°–166°C.

Analysis: Calculated for $C_{16}H_{20}N_2O_5$: C,59.99; H,6.29; N,8.75. Found: C,59.67; H,6.32; N,8.52.

EXAMPLE 8(B)

4-Amino-5-chloro-2-methoxy-N-(1-methyl-3-pyrrolidinyl)benzamide

A suspension of 5.3 g. (0.022 mole) of 4-acetamido-5-chloro-2-methoxybenzoic acid in 30 ml. of thionyl chloride was refluxed for two hours and then concentrated. To the concentrate was added 100 ml. of chloroform and the solution was again concentrated. The residue was again dissolved in chloroform and added at a rapid drop to a chloroform solution containing 2.4 g. (0.024 mole) of 3-amino-1-methylpyrrolidine. The solution was stirred for one hour and concentrated. The residue was dissolved in 100 ml. of 4N hydrochloric acid and the solution was refluxed for 10 minutes, cooled in an ice bath and basified with sodium hydroxide. The mixture was extracted with chloroform and the extract dried and concentrated. The crystalline residue was recrystallized from isopropyl ether-isopropyl alcohol followed by another recrystallization from ethyl acetate. The yield of product was 1.4 g. (22%); m.p. 185°–187°C.

Analysis: Calculated for $C_{13}H_{18}ClN_3O_2$: C,55.03; H,6.39; N,14.81. Found: C,54.94; H,6.39; N,14.72.

EXAMPLE 9

4-Methylamino-N-(1-cyclohexyl-3-pyrrolidinyl)-N-methylbenzamide Dihydrochloride

A solution of 50 ml. of thionyl chloride and 16 g. (0.065 mole) of p-(N-methyltrifluoroacetamido)benzoic acid was refluxed for 2.5 hours. The solution was concentrated under reduced pressure and the residue dissolved in 50 ml. of chloroform. After removing the chloroform under reduced pressure the residue was again dissolved in 50 ml. of chloroform and to the solution was added 13 g. (0.071 mole) of 1-cyclohexyl-3-methylaminopyrrolidine. The solution was stirred 15 minutes and washed with dilute sodium hydroxide. After evaporation of the chloroform, the residue was dissolved in 400 ml. of 3 N hydrochloride acid by heating on a steam bath for 30 minutes. The acid solution was basified with aqueous sodium hydroxide and extracted with chloroform. The extract was concentrated and the residue chromatographed on a magnesium silicate column eluting with benzene and acetone in one liter portions of % benzene/% acetone of 100/0; 99:1; 98:2; 96/4; 92/8; 84/16; 68/32; 34/66; 0/100 followed by several liters of acetone. The eluant was collected in 500 ml. fractions, fractions 18 to 24 being combined and concentrated under reduced pressure. Nuclear magnetic resonance and mass spectrum analyses indicated that the residue was the titled compound. A small portion was distilled in a molecular still.

Analysis: Calculated for $C_{19}H_{29}N_3O$: C,72.34; H,9.27; N,13.32. Found: C,72.07; H,9.22; N,12.93.

The remainder of the free base was converted to the dihydrochloride salt with ethereal hydrogen chloride in methylisobutyl ketone-ethanol. Melting point of the salt was about 205°C.

The data of additional Examples 10–49 of the present invention are given in Tables 1–3.

Table 1

N-(1-Cyclohexyl-3-pyrrolidinyl)benzamides

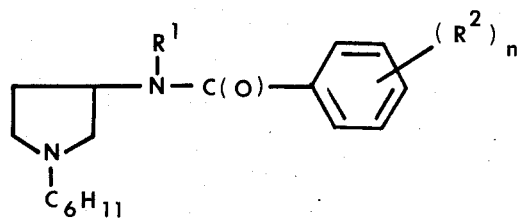

| Example No. | $R^1$ | $R^2$ | M.P. (B.P.) °C. | C Calcd. Found | H Calcd. Found | N Calcd. Found |
|---|---|---|---|---|---|---|
| 10 | H | 4-F | 135–136 | 70.32 / 70.31 | 7.98 / 7.91 | 9.65 / 9.53 |
| 11 | H | 4-Br | 151–153 | 58.13 / 57.88 | 6.60 / 6.64 | 7.97 / 7.97 |
| 12 | H | 3,5-$(NO_2)_2$ | 159–161 | 56.35 / 56.17 | 6.12 / 6.13 | 15.46 / 15.51 |
| 13 | H | 3,4-$Cl_2$ | 134–136 | 59.83 / 59.71 | 6.50 / 6.54 | 8.21 / 8.15 |
| 14 | H | 2-Br | 112–113 | 58.13 / 58.52 | 6.60 / 6.88 | 7.97 / 7.85 |
| 15 | H | 3,4-$(OC_2H_5)_2$ | 151–152 | 69.97 / 69.70 | 8.95 / 8.95 | 7.77 / 7.73 |
| 16 | H | 3-$CF_3$ | 93–95 | 63.52 / 63.34 | 6.81 / 6.92 | 8.23 / 8.17 |
| 17 | H | 4-Cl | 145–148 | 66.55 / 66.30 | 7.56 / 7.90 | 9.13 / 9.19 |
| 18 | H | 3,4,5-$(OCH_3)_3$ | 142–145 | 66.27 / 66.28 | 8.34 / 8.48 | 7.73 / 7.87 |
| 19 (a) | H | 2-Cl | 183–185 | 59.48 / 59.40 | 7.05 / 7.05 | 8.16 / 8.08 |
| 20 | H | 4-I | 155–157 | 51.27 / 51.26 | 5.82 / 5.87 | 7.03 / 6.98 |
| 21 | H | 4-$C(CH_3)_3$ | 66–68 | 76.78 / 76.39 | 9.82 / 9.90 | 8.53 / 8.18 |
| 22 (a) | $CH_3$ | 4-F | 180–182 | 63.43 / 63.25 | 7.69 / 7.75 | 8.22 / 8.26 |
| 23 (b) | H | 4-$NH_2$ | 98–100 | 66.85 / 66.51 | 8.91 / 8.74 | 13.76 / 13.73 |
| 24 | H | H | 129–130 | 74.96 / 75.20 | 8.88 / 8.83 | 10.29 / 10.28 |
| 25 | H | 4-$NO_2$ | 152–153 | 64.33 / 64.23 | 7.30 / 7.34 | 13.24 / 13.27 |
| 26 (a) | $CH_3$ | H | 201–203 | 66.96 / 66.67 | 8.43 / 8.46 | 8.68 / 8.62 |
| 27 | $CH_3$ | 4-$NO_2$ | 115–116 | 65.24 / 65.44 | 7.60 / 7.64 | 12.68 / 12.59 |
| 28 (a) | $CH_3$ | 4-Cl | 200–203 | 60.51 / 60.46 | 7.33 / 7.32 | 7.84 / 7.85 |
| 29 | H | 4-O—$(CH_2)_3CH_3$ | 127–129 | 73.22 / 72.84 | 9.36 / 9.32 | 8.13 / 8.04 |
| 30 (c) | $CH_3$ | 3-$CH_3$ | 112–115 | 66.33 / 66.60 | 7.74 / 7.88 | 6.73 / 6.55 |
| 31 | $CH_3$ | 2,4-$(OCH_3)_2$ | (265–275;4mm) | 69.33 / 69.40 | 8.73 / 8.81 | 8.09 / 7.95 |
| 32 | H | 2,4-$Cl_2$ | 122–124 | 59.83 / 59.67 | 6.50 / 6.57 | 8.21 / 8.18 |
| 33 | H | 4-$SCH_3$ | 120–123 | 67.88 / 67.39 | 8.23 / 8.20 | 8.80 / 8.74 |
| 34 (d) | H | 2,4-$(OCH_3)_2$ | 186–188 | 61.59 / 61.18 | 7.19 / 7.15 | 6.25 / 6.19 |
| 35 | H | 4-N-$(CH_3)_2$ | 138–141 | 72.34 / 71.88 | 9.27 / 9.29 | 13.32 / 12.90 |
| 36 | H | 4-$CH_3$ | 149–151 | 75.48 / 75.56 | 9.15 / 9.22 | 9.78 / 9.64 |
| 37 (d) | H | 2-$OCH_3$, 4-$NH_2$, 5-Cl | 215 decomp. | 56.47 / 55.89 | 6.46 / 6.44 | 8.98 / 8.89 |
| 38 (a) | $CH_3$ | 2,4-$NO_2$ | 245–7 decomp | 52.36 / 52.39 | 6.10 / 6.13 | 13.57 / 13.50 |
| 39 (a) | $CH_3$ | 3-Br | 183–186 | 53.81 / 53.83 | 6.52 / 6.57 | 6.97 / 6.83 |
| 40 (a) | $CH_3$ | 3-$CF_3$ | 200–202 | 58.38 / 58.44 | 6.71 / 6.78 | 7.17 / 7.04 |
| 41 (a) | $CH_3$ | 4-$CH_3$ | 187–190 | 67.74 / 67.57 | 8.68 / 8.67 | 8.32 / 8.22 |

(a) HCl salt
(b) Hydrate
(c) Maleate salt
(d) Fumarate salt

Table 2

N-(1-Phenyl-3-pyrrolidinyl)benzamides

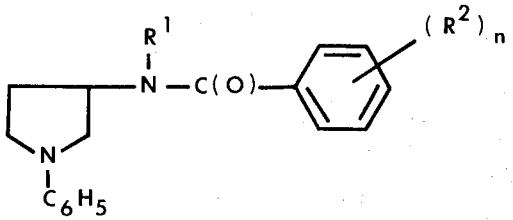

| Example No. | R¹ | R² | M.P. °C. | C Calcd. Found | H Calcd. Found | N Calcd. Found |
|---|---|---|---|---|---|---|
| 42 | $CH_3$ | 4-$NO_2$ | 149–150 | 66.44 / 66.37 | 5.89 / 5.93 | 12.92 / 12.83 |
| 43 | H | H | 153–155 | 76.66 / 76.58 | 6.81 / 6.72 | 10.52 / 10.48 |
| 44 | $CH_3$ | 4-$NH_2$ | 168–170 | 73.19 / 72.77 | 7.17 / 7.10 | 14.23 / 14.22 |
| 45 | H | 4-$NH_2$ | 213–216 | 72.57 / 72.74 | 6.81 / 6.76 | 14.94 / 15.09 |
| 46 | n-$C_4H_9$ | 4-$NH_2$ | — | 74.74 / 74.76 | 8.07 / 7.91 | 12.45 / 12.49 |

Table 3

N-(1-Phenyllower-alkyl-3-pyrrolidinyl)benzamides

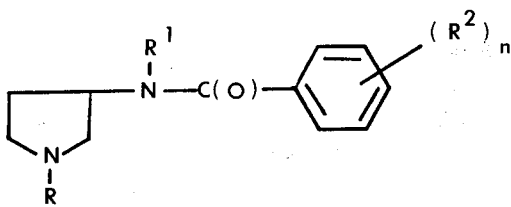

| Example No. | R¹ | R² | M.P. °C. | Analysis C Calcd. Found | H Calcd. Found | N Calcd. Found |
|---|---|---|---|---|---|---|
| 47 (a)(b) | $C_6H_5$ | 4-Cl | 152–154 | 65.52 / 65.27 | 5.50 / 5.55 | 5.66 / 5.60 |
| 48 (c)(d) | $C_6H_5$ | H | 192–193 | 73.36 / 73.11 | 6.41 / 6.47 | 7.13 / 7.02 |
| 49 (c)(d) | H | H | 208–211 | 68.24 / 68.18 | 6.68 / 6.70 | 8.84 / 8.56 |

(a) Oxalate salt
(b) P =—$CH_2CH_2$—$C_6H_5$
(c) R =—$CH_2$—$C_6H_5$
(d) Hydrochloride salt

EXAMPLE 50

N-(1-Cyclohexyl-3-pyrrolidinyl)-N-methyl-4-nitrothiobenzamide

Twenty-five grams (0.56 mole) of N-(1-cyclohexyl-3-pyrrolidinyl)-p-nitro-N-methylbenzamide fumarate was partitioned between dil. sodium hydroxide and 400 ml. benzene. The benzene solution was dried with sodium sulfate and distilled to a volume of 250 ml. To this was added a finely ground mixture of 10 g. (0.045 mole) of phosphorous pentasulfide and 10 g. of potassium sulfide. The mixture was refluxed four hours and an additional 10 g. of phosphorous pentasulfide added and refluxed two hours. The benzene was decanted off of the hard solid. The solid was partitioned between dil. sodium hydroxide and chloroform. The chloroform was dried, concentrated and the residue crystallized twice from isopropyl ether-ethyl acetate. Yield 3.77 g. (19.5%); m.p. 108°–110°C.

Analysis: Calculated for $C_{18}H_{25}N_3O_2S$: C,62.22; H,7.25; N,12.09. Found: C,62.15; H,7.25; N,12.07.

Procedure B

A mixture of 18.2 g. (0.10 mole) of 1-cyclohexyl-3-methylaminopyrrolidine, 16.5 g. (0.11 mole) of p-nitrobenzaldehyde and 4.0 g. (0.125 gram atom) of sulfur was heated at 80°C. for 1.0 hour. The reaction mixture was treated with 200 ml. of ethyl acetate, charcoal was added and the mixture filtered. The filtrate was concentrated and the residual material was recrystallized twice from isopropyl alcohol-ethyl acetate. The yield of product (m.p. 98°–102°C.) was 3.8 g. (10%). The melting point was raised to 108°–110°C. by further recrystallization.

EXAMPLE 51

4-Amino-N-(1-cyclohexyl-3-pyrrolidinyl)-N-methylthiobenzamide Maleate

A suspension of 5.7 g. (0.016 mole) of N-(1-cyclohexyl-3-pyrrolidinyl)-N-methyl-4-nitrothiobenzamide in 600 ml. of ethanol was shaken 5 hrs. with Rh/Al and water in a Parr bomb. No hydrogen uptake was observed. The mixture was filtered and treated with Rh/Al and again shaken in water at 45 psi. at room temperature for 18 hrs. and filtered. The filtrate was concentrated and the residue chromatographed on a 4.5 × 60 cm. silica gel (CC7 100–200 mesh) column, eluting with the following:

| Volume | % $CHCl_3$ | % $CH_3OH$ |
|---|---|---|
| 1 liter | 100 | 0 |
| 0.5 liter | 99 | 1 |
| 0.5 liter | 98 | 2 |
| 3 liters | 96 | 4 |

After 3 liters of eluent was collected and discarded, the fourth liter contained the desired product. The maleate salt was prepared and crystallized from isopropyl alcohol. Yield 0.9 g. (13%); m.p. 138°–141°C.

Analysis: Calculated for $C_{22}H_{31}N_3O_4S$: C,60.95; H,7.21; N,9.69. Found: C,60.11; H,7.27; N,9.33.

EXAMPLE 52

4-Amino-N-(1-cyclohexyl-3-pyrrolidinyl)-N-methylthiobenzamide

The compound was prepared as described in Example 51, but instead of forming a salt the base was distilled on the molecular still at about 200°C. and 0.01 mm. Analysis: Calculated for $C_{18}H_{27}N_3S$: C,68.10; H,8.57; N,13.24. Found: C,68.33; H,8.63; N,13.43.

EXAMPLE 53

N-(1-Cyclohexyl-3-pyrrolidinyl)-2-methoxy-5-sulfamoylbenzamide

To 3.7 g. (0.022 mole) of 3-amino-1-cyclohexylpyrrolidine in 100 ml. of pyridine was added dropwise with cooling 1.1 g. (0.008 mole) of phosphorous trichloride at 20°C. After stirring one hour, 3 g. (0.013 mole) of 2-methoxy-5-sulfamoylbenzoic acid was added and refluxed 6 hrs. The solution was concentrated and the residue partitioned between dilute hydrochloride acid and isopropyl ether. The acid was made basic with ammonium hydroxide and extracted with chloroform which was dried (sodium sulfate) and concentrated. The residue was crystallized from ethyl acetate and recrystallized from isopropyl alcohol. Yield 1 g. (33%); m.p. 184°–187°C.

Anaylsis: Calculated for $C_{18}H_{27}N_3O_4S$: C,56.67; H,7.13; N,11.02. Found: C,56.39; H,7.09; N,11.00.

Examples 54–67 were prepared by procedures described hereinabove. In all cases R is cyclohexyl except as noted.

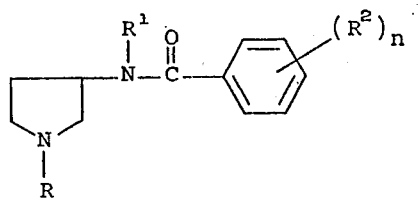

| Example No. | R¹ | R² | M.P. °C. | C Calcd. Found | H Calcd. Found | N Calcd. Found |
|---|---|---|---|---|---|---|
| 54 (a) | $CH_3$ | 3,5-$NO_2$ | 228–31 | 52.36 52.08 | 6.10 6.16 | 13.57 13.39 |
| 55 (a) | $CH_3$ | 3,4-$OC_2H_5$ | | 64.30 64.24 | 8.58 8.54 | 6.82 6.72 |
| 56 (a) | $CH_3$ | 4-$SCH_3$ | 196–8 | 61.85 61.69 | 7.92 7.89 | 7.59 7.48 |
| 57 | H | 3-$OCH_2C_6H_5$ | 119–20 | 76.16 75.87 | 7.99 8.09 | 7.40 7.28 |
| 58 | H | 3-OH | 210–11 | 70.80 70.50 | 8.39 8.24 | 9.71 9.53 |
| 59 | $CH_3$ | 3-OH | 130–2 | 71.49 71.23 | 8.67 8.67 | 9.26 9.26 |
| 60 (a) | H | 4-CN | 198–200 | 64.76 64.78 | 7.25 7.35 | 12.59 12.56 |
| 61 (a) | $CH_3$ | 4-CN | 194–5 | 65.60 65.20 | 7.53 7.55 | 12.08 12.03 |
| 62 (a) | $CH_3$ | 4-$OCH_3$ | 170–3 | 64.67 64.55 | 8.28 8.12 | 7.94 7.85 |
| 63 (b) | $CH_3$ | 2-$OCH_3$ 4-$NH_2$ 5-Cl | 195–8 | 39.34 39.52 | 5.91 5.71 | 7.24 6.82 |
| 64 (c,e) | $CH_3$ | 4-$NO_2$ | 157–60 | | | |
| 65 (e,d) | $CH_3$ | 4-$NH_2$ | 179–80 | 59.20 58.93 | 8.21 8.20 | 12.01 12.06 |
| 66 (a,f) | $CH_3$ | 4-$NO_2$ | | | | |
| 67 (f) | $CH_3$ | 4-$NH_2$ | 123–5 | 74.76 74.77 | 10.20 10.28 | 10.90 10.81 |

(a) Hydrochloride salt
(b) Disulfate monohydrate
(c) Fumarate salt
(d) Cyclohexanesulfamate salt
(e) R is cyclopentyl
(f) R is cyclododecyl

EXAMPLE 68

(−)
4-Amino-N-(1-cyclohexyl-3-pyrrolidinyl)-N-methylbenzamide Malate

An ethanol solution containing 20.0 g. (0.067 mole) of 4-amino-N-(1-cyclohexyl-3-pyrrolidinyl)-N-methylbenzamide (free base of Example 4) was treated with 4.94 g. (0.037 mole) of 1-malic acid and the solution was refrigerated overnight. The crystalline material which separated (m.p. 147°–157°C.) was recrystallized twice from ethanol to give 5.0 g. of crystals which melted at 161°–163°C. $[\alpha]_D^{30} = -22.65$.

Analysis: Calculated for $C_{22}H_{33}N_3O_6$: C,60.67; H,7.64; N,9.65. Found: C,60.25; H,7.61; N,9.64.

EXAMPLE 69

(+)
4-Amino-N-(1-cyclohexyl-3-pyrrolidinyl)-N-methylbenzamide Malate

The mother liquor and filtrates from Example 68 were combined, 2.0 g. of d-malic acid added, and the solution refrigerated overnight. The liquid-solid mixture was filtered, the solid discarded and the filtrate concentrated. The concentrated residue was partitioned between chloroform and dilute sodium hydroxide, the separated chloroform layer concentrated and the residue treated with 2.0 g. of d-malic acid in ethanol. The separated crystals after recrystallization from ethanol weighed 2.2 g. and melted at 161°–163°C. $[\alpha]_D^{30} = +24.81$.

Analysis: Calculated from $C_{22}H_{33}N_3O_6$: C,60.67; H,7.64; N,9.65. Found: C,60.41; H,7.66; N,9.64.

EXAMPLE 70

(−)
4-Amino-N-(1-cyclohexyl-3-pyrrolidinyl)-N-methylbenzamide Fumarate

An aqueous solution containing 3.9 g. (0.0094 mole) of (−) 4-amino-N-(1-cyclohexyl-3-pyrrolidinyl)-N-methylbenzamide malate (Example 68) was extracted with chloroform, the chloroform solution was dried over sodium sulfate and concentrated. The residue was dissolved in ethanol, 1.2 g. (0.01 mole) of fumaric acid added and the solution refrigerated. The fumarate salt which separated weighed 3.3 g. and melted at 205°–207°C. $[\alpha]_D^{30} = -13.89$.

Analysis: Calculated for $C_{22}H_{31}N_3O_5$: C,63.29; H,7.48; N,10.06. Found: C,63.12; H,7.47; N,10.11.

EXAMPLE 71

(+)
4-Amino-N-(1-cyclohexyl-3-pyrrolidinyl)-N-methyl-benzamide Fumarate

An aqueous solution of 2.2 g. (0.005 mole) of (+) 4-amino-N-(1-cyclohexyl-3-pyrrolidinyl)-N-methyl-benzamide maleate was made basic using sodium hydroxide and the basic solution was extracted with chloroform. The dried chloroform solution was concentrated and the residue treated with a solution of 0.6 g. (0.005 mole) of fumaric acid in ethanol-methanol. The fumarate salt which separated weighed 1.6 g. and melted at 204°–206°C. $[\alpha]_D^{30} = +12.72$.

Analysis: Calculated for $C_{22}H_{31}N_3O_5$: C,63.29; H,7.48; N,10.06. Found: C,63.71; H,7.39; N,9.85.

PHARMACOLOGY

The anti-emetic properties of the compounds of Formulae I and II were established using a modification of the methods of Chen and Ensor, J. Pharmac. Exp. Ther. 98: 245–250 (1950) and of Leonard et al, J. Pharmac. Exp. Ther. 154, 339–345 (1966). Drug activity was assessed by its ability to reduce the frequency of apomorphine-induced emesis in dogs. The dogs were prescreened for fairly constant emetic responses to the subcutaneous administration of 0.1 mg./kg. of apomorphine hydrochloride, and those which vomited five or more times in the 40-minute period after apomorphine administration were selected for drug studies.

Groups of three dogs were used in preliminary tests and for the determinations of time of peak drug effect. Dose response curves were usually obtained using four drug-treated groups; each group contained at least three dogs. The dogs were fed approximately 17 hours prior to a test. Drugs were administered and at suitable intervals the dogs received 0.1 mg/kg of apomorphine hydrochloride subcutaneously. Frequency of emesis was determined during the next 40 minutes and emesis was counted as the actual expulsion of stomach contents.

In oral studies, drugs were administered in gelatin capsules (controls received an empty capsule). In the subcutaneous studies, drugs were administered in distilled water and/or polyethylene glycol-300.

Dogs were re-used at intervals of not less than one week. The $ED_{50}$ is the dose which reduces the frequency of emesis of drug treated dogs to a value 50% below that of controls. Mean frequency of emesis for each drug treated group was compared with a mean control value derived by pooling the prior control emetic frequencies for all dogs used on that test day. The difference is expressed as a percentage decrease relative to controls. The per cent decrease in mean frequency of emesis for each drug-treated group (ordinate) was plotted against log dose (abscissa) on semi-log graph sheets. The $ED_{50}$ was calculated by the method of Goldstein (Biostatistics, An Introductory Test; Pages 156–161; The MacMillan Co., New York, 1964).

Effectiveness of the compositions of this invention in treating emesis is illustrated in the following examples having the suffix "p" which refers to the pharmacological nature of the examples and distinguishes them from the foregoing chemical examples which make up the compositions.

EXAMPLE 1P

Three dogs selected as described above were injected subcutaneously with 5.0 mg./kg. (3.12 mg./kg. expressed as free base) of the test drug 4-amino-N-(1-cyclohexyl-3-pyrrolidinyl)-N-methyl-benzamide cyclohexane-sulfamate from compound Example 4. One hour later apormorphine hydrochloride was administered in doses of 0.1 mg./kg. subcutaneously. Complete blockage of emesis (—100%) was observed over the 40-minute period following administration of apomorphine hydrochloride. Lower doses of the test drug were administered and tested in like manner on other groups of dogs to establish the dose response curve from which the $ED_{50}$ of 0.43 mg./kg. (0.27 mg./kg. expressed as free base) was established for subcutaneous administration of the test drug.

EXAMPLE 2P

Using the technique described in the foregoing general procedure and pharmacology in Example 1 for subcutaneous evaluation of test drugs against apomorphine induced emesis, results for additional compounds were obtained as shown in Table 4.

Table 4

| Anti-Emetic Effect of Subcutaneous Administration (doses expressed as free base) | |
|---|---|
| Example | $ED_{50}$, mg./kg. |
| 1 | 0.40 |
| 2 | 1.60 |
| 3(a) | — |
| 6 | 1.10 |
| 7 | 2.40 |
| 9 | 0.50 |
| 10 | 0.15 |
| 11 | 0.70 |
| 12 | 0.15 |
| 13 | 0.28 |
| 15 | 0.66 |
| 16 | 0.18 |
| 17 | 0.28 |
| 18 | 0.40 |
| 20 | 1.25 |
| 23 | 1.67 |
| 24 | 0.28 |
| 25 | 2.03 |
| 32 | 2.40 |
| 33 | 0.88 |
| 34 | 0.026 |
| 35 | 0.89 |
| 36 | 0.31 |
| 37 | 0.003 |

(a)A 50% reduction in emesis was obtained at a dose level of 5 mg./kg.

EXAMPLE 3P

Capsules containing the test drug 4-amino-N-(1-cyclohexyl-3-pyrrolidinyl)-N-methylbenzamide cyclohexanesulfamate from compound Example 4 were administered orally to dogs at a dosage of 2.5 mg./kg. After two hours the dogs were injected subcutaneously with 0.1 mg./kg. apomorphine hydrochloride dissolved in water. There was almost complete blockage (—95% of apomorphine induced emesis. Lower doses of test drug were administered and tested in like manner on other groups of dogs to establish the dose response curve from which the oral $ED_{50}$ of 0.22 mg./kg. was established.

EXAMPLE 4P

Using the techniques described in the foregoing general procedure and in pharmacology Example 3 for oral evaluation of test drugs against apomorphine induced emesis, additional results in Table 5 were obtained.

Table 5

| Anti-Emetic Effect of Oral Administration (doses expressed as free base) | |
|---|---|
| Example | $ED_{50}$, mg./kg. |
| 10 | 1.5 |
| 23 | 2.5 |
| 24 (a) | — |

(a) A 60% reduction in emesis was obtained at a dose level of 5 mg./kg.

EXAMPLE 5P

The potentiating effect on anti-emesis observed when the pyrrolidinyl nitrogen atom was substituted with the cyclohexyl radical as compared to an alkyl radical is shown in Table 6.

Table 6

| Comparison of Anti-Emetic Effect of Cyclohexyl vs. Lower-alkyl Substitution on Pyrrolidine Nitrogen | | | | |
|---|---|---|---|---|
| Example | R | $R^1$ | $R^2$ | Anti-Apomorphine Effect (as Free Base) $ED_{50}$, mg./kg. (a) |
| 37 | $C_6H_{11}$ | H | 2-$OCH_3$, 4-$NH_2$, 5-Cl | 0.003 |
| 8B | $CH_3$ | H | 2-$OCH_3$, 4-$NH_2$, 5-Cl | 0.053 |
| 24 | $C_6H_{11}$ | H | H | 0.28 |
| 8A | $CH_3$ | H | H | 3.2 |

(a) Subcutaneous administration in dogs.

EXAMPLE 6P

The effects observed in reducing catalepsy in rats noted when the amido nitrogen was substituted with an alkyl radical are illustrated in Table 7.

Table 7

| Reduction of Catalepsy by Amido Nitrogen Substitution | | | | | |
|---|---|---|---|---|---|
| Example | R | $R^1$ | $R^2$ | Anti-Apomorphine Effect (As Free Base) $ED_{50}$, mg/kg (a) | Catalepsy (As Free Base) $ED_{50}$ or other mg/kg (b) |
| 4 | $C_6H_{11}$ | $CH_3$ | 4-$NH_2$ | 0.27 | no catatonia to 125 |
| 23 | $C_6H_{11}$ | H | 4-$NH_2$ | 1.7 | 33% at 94.2 |
| 27 | $C_6H_{11}$ | $CH_3$ | 4-$NO_2$ | 10.0 | no catatonia to 100 (lethal dose) |
| 25 | $C_6H_{11}$ | H | 4-$NO_2$ | 1.8 | 28 |

(a) Subcutaneous administration in dogs.
(b) IP administration in rats.

Absence of catatonia in rats is indicative of a high degree of selectivity in anti-emetic drugs and in particular indicates an absence of undesirable tranquilizing property.

Procedure For Determining Catalepsy in Rats

Drugs were blind tested with positive and negative controls. The procedure used is a modification of the method previously described by Tedeschi et al., Archs. Int. Pharmacodyn. Ther. 122, 129–143 (1959). The modified procedure is as follows.

Groups of six rats are dosed (IP) with drugs in saline solution and tested hourly over a six hour period. A phenothiazine or non-phenothiazine reference standard is tested concomitantly as a positive control; negative controls receive only the saline vehicle. After administration the rats are positioned hourly with each foot on a No. 7 rubber stopper. A rat is considered cataleptic if it remains immobile on the stoppers for five seconds or longer at two or more consecutive hourly observation intervals. The percentages of rats which are cataleptic at various dosage levels are noted and, where feasible, these data are used to determine the $ED_{50}$ by the method of Litchfield and Wilcoxon, J. Pharmac. Exp. Ther. 96, 99–113 (1949).

The pharmaceutical compositions of this invention comprise compounds of Formula I above in an amount to provide anti-emetic action. The compositions contain 1.0 mg. to 100 mg. active medicament per unit dose. Preferably, the compositions contain from about 5 mg. to 100 mg. of medicament, advantageously from about 5 mg. to about 50 mg. per unit dose.

The pharmaceutical carrier employed in the composition can be either solid or liquid. Exemplary of solid carriers are lactose, magnesium stearate, terra alba, sucrose, talc, stearic acid, gelatin, agar, pectin or acacia. Exemplary of liquid carriers are vegetable oils and water. Similarly, the carrier or diluent may include a sustained release material such as glyceryl monostearate or glyceryl distearate alone or with a wax.

A wide variety of pharmaceutical forms can be employed by methods well known to the art. Thus, if a solid carrier is used the composition can be tableted or prepared as a powder, a troche, a lozenge or a suppository. Gelatin capsules containing the medicament can also be prepared. If a liquid carrier is used, the composition can be in the form of a soft gelatin capsule, a liquid suspension or a syrup. Parenteral dosage forms are obtained by dissolving a water-soluble salt of the active antiemetic agent in water or saline solution in a concentration such that 1 cc. of the solution contains from 1.0 mg. to 25 mg. of active antiemetic agent. The solution can then be filled into single or multiple dose ampules.

The method in accordance with this invention comprises administering internally to warm blooded animals including human beings certain N-(1-substituted-3-pyrrolidinyl)benzamides and thiobenzamides or a nontoxic organic or inorganic acid addition salt thereof, preferably with a nontoxic pharmaceutical carrier such as described above, in an amount sufficient to control nausea and vomiting. The active antiemetic agent is administered orally or parenterally in repeated doses until satisfactory response is obtained. The daily dosage is from about 10 mg. to about 300 mg. of active medicament, advantageously from about 5 mg. to 50 mg. When the method described above is carried out, nausea and vomiting is controlled rapidly and effectively.

What is claimed is:

1. A method of treating warm blooded animals for emesis which comprises internally administering from about 5 mg. to about 100 mg. of an antiemetic selected from the group having the following structural formula:

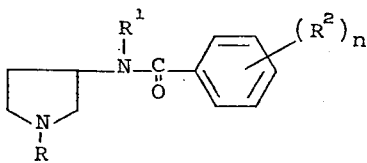

wherein;

R is selected from the group consisting of cycloalkyl of 4 to 12 carbon atoms, phenyl, benzyl and phenethyl, $R^1$ is selected from the group consisting of hydrogen, lower alkyl of 1 to 8 carbon atoms and phenyl, $R^2$ is selected from the group consisting of halogen, loweralkyl of 1 to 8 carbon atoms, methoxy, ethoxy, amino, nitro, dimethylamino, methylamino, mercaptomethyl, acetamido, sulfamoyl, cyano, hydroxy, benzyloxy and trifluoromethyl, n is an integer from zero to three inclusive, and the pharmaceutically acceptable acid addition salts thereof.

2. The method as defined in claim 1 wherein R is cyclohexyl.

3. The method as defined in claim 1 wherein R is cyclohexyl and $R^1$ is lower alkyl of 1 to 8 carbon atoms.

4. The method in accordance with claim 1 in which the administration is orally to human beings.

5. The method as defined in claim 1 wherein the antiemetic is N-(1-cyclohexyl-3-pyrrolidinyl)-3-bromobenzamide.

6. The method as defined in claim 1 wherein the antiemetic is N-(1-cyclohexyl-3-pyrrolidinyl)-2-fluorobenzamide.

7. The method as defined in claim 1 wherein the antiemetic is N-(1-cyclohexyl-3-pyrrolidinyl)-2-methoxy-5-sulfamoylbenzamide.

8. The method as defined in claim 1 wherein the antiemetic is 4-amino-N-(1-cyclohexyl-3-pyrrolidinyl)-N-methylbenzamide.

9. The method as defined in claim 1 wherein the antiemetic is N-(1-cyclohexyl-3-pyrrolidinyl)-p-dimethylamino-N-methylbenzamide.

10. The method as defined in claim 1 wherein the antiemetic is N-(1-cyclohexyl-3-pyrrolidinyl)-4-acetamidobenzamide.

11. The method as defined in claim 1 wherein the antiemetic is 4-methylamino-N-(1-cyclohexyl-3-pyrrolidinyl)-N-methylbenzamide.

12. The method as defined in claim 1 wherein the antiemetic is N-(1-cyclohexyl-3-pyrrolidinyl)-4-fluorobenzamide.

13. The method as defined in claim 1 wherein the antiemetic is N-(1-cyclohexyl-3-pyrrolidinyl)-4-bromobenzamide.

14. The method as defined in claim 1 wherein the antiemetic is N-(1-cyclohexyl-3-pyrrolidinyl)-3,5-dinitrobenzamide.

15. The method as defined in claim 1 wherein the antiemetic is N-(1-cyclohexyl-3-pyrrolidinyl)-3,4-dichlorobenzamide.

16. The method as defined in claim 1 wherein the antiemetic is N-(1-cyclohexyl-3-pyrrolidinyl)-3,4-diethoxybenzamide.

17. The method as defined in claim 1 wherein the antiemetic is N-(1-cyclohexyl-3-pyrrolidinyl)-3-trifluoromethylbenzamide.

18. The method as defined in claim 1 wherein the antiemetic is 4-chloro-N-(1-cyclohexyl-3-pyrrolidinyl)-benzamide.

19. The method as defined in claim 1 wherein the antiemetic is N-(1-cyclohexyl-3-pyrrolidinyl)-3,4,5-trimethoxybenzamide.

20. The method as defined in claim 1 wherein the antiemetic agent is N-(1-cyclohexyl-3-pyrrolidinyl)-4-iodobenzamide.

21. The method as defined in claim 1 wherein the antiemetic is p-amino-N-(1-cyclohexyl-3-pyrrolidinyl)-benzamide.

22. The method as defined in claim 1 wherein the antiemetic is N-(1-cyclohexyl-3-pyrrolidinyl)benzamide.

23. The method as defined in claim 1 wherein the antiemetic is N-(1-cyclohexyl-3-pyrrolidinyl)-4-nitrobenzamide.

24. The method as defined in claim 1 wherein the antiemetic is N-(1-cyclohexyl-3-pyrrolidinyl)-2,4-dichlorobenzamide.

25. The method as defined in claim 1 wherein the antiemetic is N-(1-cyclohexyl-3-pyrrolidinyl)-4-(methylthio)benzamide.

26. The method as defined in claim 1 wherein the antiemetic is N-(1-cyclohexyl-3-pyrrolidinyl)-2,4-dimethoxybenzamide.

27. The method as defined in claim 1 wherein the antiemetic is N-(1-cyclohexyl-3-pyrrolidinyl)-4-dimethylaminobenzamide.

28. The method as defined in claim 1 wherein the antiemetic is N-(1-cyclohexyl-3-pyrrolidinyl)-4-methylbenzamide.

29. The method as defined in claim 1 wherein the antiemetic is 4-amino-5-chloro-N-(1-cyclohexyl-3-pyrrolidinyl)-2-methoxybenzamide.

30. A method of treating warm blooded animals for emesis which comprises internally administering from about 5 mg. to about 100 mg. of an antiemetic selected from the group having the following structural formula:

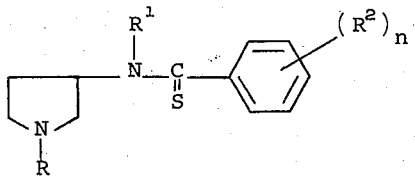

wherein;

R is cycloalkyl of 4 to 12 carbon atoms,

R¹ is hydrogen and lower alkyl of 1 to 8 carbon atoms,

R² is nitro, amino, halogen, sulfamoyl, methoxy and ethoxy, n is an integer from zero to three inclusive, and pharmaceutically acceptable acid addition salts thereof.

31. The method as defined in claim 30 wherein the antiemetic is 4-amino-N-(1-cyclohexyl-3-pyrrolidinyl)-N-methylthiobenzamide.

32. The method as defined in claim 30 wherein the antiemetic is 4-nitro-N-(1-cyclohexyl-3-pyrrolidinyl)-N-methylthiobenzamide.

33. A pharmaceutical composition having antiemetic activity, said composition in unit dosage form comprising a pharmaceutical carrier and from about 1 mg. to about 200 mg. of an antiemetic selected from the group having the following structural formula:

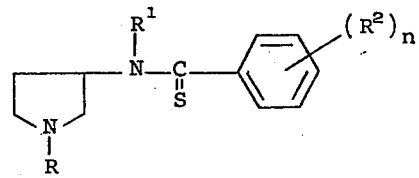

wherein;

R is cycloalkyl of 4 to 12 carbon atoms,

R¹ is hydrogen and lower alkyl of 1–8 carbon atoms,

R² is nitro, amino, halogen, sulfamoyl methoxy and ethoxy, n is an integer from zero to three inclusive, and the pharmaceutically acceptable acid addition salts thereof.

* * * * *